United States Patent
Kang et al.

(10) Patent No.: US 10,871,429 B2
(45) Date of Patent: Dec. 22, 2020

(54) INJECTION APPARATUS AND INJECTION METHOD FOR LIQUID SAMPLE FOR STANDARD GAS PRODUCTION

(71) Applicant: KOREA RESEARCH INSTITUTE OF STANDARDS AND SCIENCE, Daejeon (KR)

(72) Inventors: Jihwan Kang, Gyeongsangnam-do (KR); Yong-Doo Kim, Daejeon (KR); Sangil Lee, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 16/336,818

(22) PCT Filed: Jul. 13, 2018

(86) PCT No.: PCT/KR2018/007951
§ 371 (c)(1),
(2) Date: Mar. 26, 2019

(87) PCT Pub. No.: WO2019/017655
PCT Pub. Date: Jan. 24, 2019

(65) Prior Publication Data
US 2019/0226950 A1 Jul. 25, 2019

(30) Foreign Application Priority Data
Jul. 17, 2017 (KR) .......... 10-2017-0090397

(51) Int. Cl.
*G01N 1/38* (2006.01)
*B01L 5/02* (2006.01)
(Continued)

(52) U.S. Cl.
CPC ............... *G01N 1/38* (2013.01); *B01L 5/02* (2013.01); *G01N 33/0011* (2013.01);
(Continued)

(58) Field of Classification Search
CPC .. G01N 1/38; G01N 33/0011; G01N 33/0018; G01N 2001/2893; G01N 2001/396; G01N 2001/387; B01L 5/02
See application file for complete search history.

(56) References Cited

U.S. PATENT DOCUMENTS 4,000,654 A * 1/1977 Harris, Jr. .......... G01N 35/1079
73/863.81
4,896,545 A * 1/1990 Averette .............. B01L 3/0241
422/930
(Continued)

FOREIGN PATENT DOCUMENTS

JP 4361936 B2 11/2009
JP 2016-200562 A 12/2016
(Continued)

*Primary Examiner* — Nicolas A Arnett
(74) *Attorney, Agent, or Firm* — Nixon Peabody LLP; Thomas P. Pavelko

(57) ABSTRACT

The purpose of the present invention is to provide an injection apparatus and an injection method for a liquid sample for standard gas production, wherein the injection apparatus for injecting a liquid sample present in a liquid state at room temperature into a standard gas container has an improved structure that minimizes the area in which the liquid sample directly contacts the injection apparatus so as to prevent the problem in which the liquid sample is adsorbed into the injection apparatus. Furthermore, another purpose of the present invention is to provide an injection apparatus and an injection method for a liquid sample for standard gas production, in which a step of volatilizing the remaining liquid sample by heating is eliminated during the injection of the liquid sample, thereby preventing the appa-
(Continued)

ratus from being damaged by heating to thereby improve the durability of the apparatus.

9 Claims, 7 Drawing Sheets

(51) Int. Cl.
  *G01N 33/00* (2006.01)
  *G01N 1/28* (2006.01)
(52) U.S. Cl.
  CPC . *G01N 33/0018* (2013.01); *G01N 2001/2893* (2013.01); *G01N 2001/386* (2013.01); *G01N 2001/387* (2013.01)

(56) References Cited

U.S. PATENT DOCUMENTS

| | | | | |
|---|---|---|---|---|
| 5,992,214 A * | 11/1999 | Schlitt | ................ | G01N 33/0013 73/23.35 |
| 6,649,129 B1 * | 11/2003 | Neal | ..................... | G01N 1/16 422/88 |
| 8,247,239 B2 * | 8/2012 | Tipler | ................... | G01N 30/24 436/174 |
| 2018/0158659 A1 * | 6/2018 | Zhang | ..................... | G01N 1/10 |

FOREIGN PATENT DOCUMENTS

| | | |
|---|---|---|
| KR | 10-0656415 A | 12/2006 |
| KR | 10-2018-0056357 A | 6/2008 |
| KR | 10-2016-0021349 A | 2/2016 |
| WO | WO-2018208042 A1 * | 11/2018 ............... G01N 1/38 |

* cited by examiner

10,871,429 B2

INJECTION APPARATUS AND INJECTION METHOD FOR LIQUID SAMPLE FOR STANDARD GAS PRODUCTION

CROSS-REFERENCE TO RELATED APPLICATIONS

This application is the 35 U. S. C. § 371 National Stage patent application of International Application No.: PCT/KR2018/007951, filed Jul. 13, 2018, entitled, INJECTION APPARATUS AND INJECTION METHOD FOR LIQUID SAMPLE GAS PRODUCTION, the entire disclosure of which is herein incorporated by reference.

TECHNICAL FIELD

The present invention relates to a liquid sample injection apparatus and injection method for preparation of standard gas, and more particularly, to a liquid sample injection apparatus and injection method for preparation of standard gas that minimizes a problem that a liquid sample is adsorbed to the injection apparatus by improving a conventional structure, in the injection apparatus for injecting the liquid sample that exists in a liquid state at room temperature into a standard gas container.

A reference material is a substance that may become a standard as a chemical species, similar to a prototype in a meteorological form, and in most cases, refers to a pure substance. Since the reference material is a standard for analysis, investigation, and testing of the substance, such a reference material is essential for analysis and testing that require particularly high accuracy and precision. Under room temperature and normal pressure conditions, the reference material may also have various phases in solid, liquid, and gaseous states, depending on the type of material.

In particular, it is important that the reference material in the liquid or gaseous state is not mixed or reacted with other substances. It is common to store the liquid in an ampoule (a glass container with one end stretched to be thin and long) made of special glass with a very low alkaline melting property, and to store the gas in a small bomb called a cell. In particular, since there is a high risk that other substances are mixed or the reaction occurs during a process of containing the gas reference material in the container, there are many cases in which it is necessary to pay close attention to the process of correctly containing the gas reference material in the container.

Meanwhile, in the case of the liquid or the gas, as described above, since the container itself containing the liquid or the gas is also often important, the term "gas reference material" or "standard gas" may also be used literally as a term referring to "ultra-high purity gas" itself or may also be used to refer to "container containing gas (ultra-high purity gas), which is the reference material".

BACKGROUND ART

When a standard gas of a compound that exists in a liquid state at room temperature needs to be prepared, a method of introducing a liquid raw material into a container to induce volatilization to make the liquid raw material into a gas state and filling a material of the gas state in the container is used. Korean Patent No. 0656415 ("Liquid Injection apparatus for Preparation of Standard Gas", 2006 Dec. 5, hereinafter referred to as 'Related Art Document') discloses in detail a technique for preparing standard gas of an organic compound that exists in a liquid phase.

In the related art document, a liquid injection apparatus and injection method for preparation of standard gas in preparing the standard gas of a substance that exists in a liquid phase at room temperature such as a volatile organic compound is disclosed, comprising: a standard gas preparation system for vacuum evacuation, a diluting gas cylinder for diluting a substance in a gas phase, a syringe for injecting a liquid sample to be a raw material of the standard gas to be prepared, and a heating metal body for heating the liquid sample in a process of injecting the liquid sample to volatilize the liquid sample into a gas phase. By using the device and method according to the related art document, the liquid sample in the syringe may be safely injected into the standard gas container.

Meanwhile, in such an injection process, ideally, the entire volume of the liquid sample should be completely volatilized and injected into the standard gas container, but actually, a portion of the liquid sample may be deposited and left inside the injection apparatus, particularly, inside a syringe needle which is directly used for injection. In order to prevent such a problem, in the related art document, the heating metal body is provided so as to surround the syringe needle, and the syringe needle is heated using the heating metal body, such that the liquid sample which is deposited inside the needle is completely volatilized to prevent a leakage of the liquid sample.

However, in a process of volatilizing a left liquid sample using heat as in the related art document, when a heating temperature is excessively increased, there is a risk of damaging a rubber septum used for sealing. In addition, in order to minimize the extent to which the liquid sample is deposited inside the needle, a surface of the device was subjected to special coating treatment, but there was also a problem that the cost of manufacturing the device by such treatment is increased.

RELATED ART DOCUMENT

Patent Document

1. Korean Patent No. 0656415 ("Liquid Injection apparatus for Preparation of Standard Gas", 2006 Dec. 5)

DISCLOSURE

Technical Solution

An object of the present invention is to provide a liquid sample injection apparatus and injection method for preparation of standard gas having an improved structure that minimizes a region at which a liquid sample is in direct contact with the injection apparatus to prevent a problem that the liquid sample is adsorbed to the injection apparatus, in the injection apparatus for injecting the liquid sample that exists in a liquid state at room temperature into a standard gas container. Another object of the present invention is to provide a liquid sample injection apparatus and injection method for preparation of standard gas that prevents damage of the injection apparatus itself by heating to improve durability of the device by eliminating a process of volatilizing the left liquid sample by heating during the injection of the liquid sample.

In one general aspect, a liquid sample injection apparatus 100 for preparation of standard gas that is connected to an inlet of a standard gas container 500 to supply a liquid sample and diluting gas to the inlet of the standard gas container 500 and gasifies the liquid sample to inject the gasified liquid sample to the standard gas container 500, includes: a syringe 110 including a needle 115 to inject the liquid sample; a liquid injection part 120 connected to the inlet of the standard gas container 500 extending in a vertical direction, and including a penetration path 125 extending in a horizontal direction so that the needle 115 penetrates therethrough and communicating with the inlet of the standard gas container 500; and a standard gas preparation device 130 connected to the inlet of the standard gas container 500 through a gas transfer passage 132 which is in communication with the penetration path 125 to inject a diluting gas supplied from a diluting gas cylinder 131 or to perform a vacuum evacuation of the standard gas container 500.

The needle 115 may be disposed so that a tip thereof inserted into the inlet of the standard gas container 500 is positioned at the center of the inlet of the standard gas container 500.

The needle 115 may be formed in the form of a tube having a closed tip inserted into the inlet of the standard gas container 500, and the tip may be provided with a discharge hole 115*a*. The discharge hole 115*a* may be formed below the tip of the needle 115 so as to downward vertically discharge the liquid sample.

The liquid injection part 120 may include a body part 121 having the penetration path 125 formed therein, a container connection part 122 connecting one end of the body part 121 and the inlet of the stand gas container 500 to each other, and a syringe connection part 123 connecting the other end of the body part 121 and the syringe 110 to each other. The liquid injection part 120 may further include a septum 124 embedded in the syringe connection part 123 and having a through hole formed at the center thereof so that the needle 115 penetrates therethrough to perform sealing. The syringe connection part 123 is formed in the form of a lock nut.

The gas transfer passage 132 is provided with a control valve 133 for controlling the injection of diluting gas or the performance of the vacuum evacuation.

In another general aspect, a injection method for liquid for standard gas production using the liquid sample injection apparatus 100 for preparation of standard gas as described above includes: evacuating the liquid injection part 120, the standard gas preparation device 130, and standard gas container 500; collecting the liquid sample in the syringe 110; replacing the needle 115 of the syringe 110; measuring a mass of the syringe 110 in which the liquid sample is contained; inserting the needle 115 into the penetration path 125 of the liquid injection part 120 to position the tip of the needle 115 in the inlet of the standard gas container 500; evacuating the needle 115; volatilizing and gasifying the liquid sample contained in the syringe 110 while injecting into the standard gas container 500; calculating an injection amount of the liquid sample by measuring the mass of the syringe 110 after the liquid sample is injected; and injecting the diluting gas into the standard gas container 500 through the standard gas preparation device 130.

Advantageous Effects

According to the present invention, in the process of injecting the liquid sample that exists in the liquid state at room temperature into the standard gas container, the region at which the liquid sample is in direct contact with the injection apparatus is minimized by a structural improvement of the device itself, thereby making it possible to effectively remove the problem that the liquid sample is adsorbed to the injection apparatus or is left in the injection apparatus.

In addition, by such a structural improvement, a conventional process of heating the left liquid sample to forcibly volatize the left liquid sample may be eliminated, and the damage of the device itself by heating may be prevented to thereby improve the durability of the device.

As well, conventionally, since a surface of the device was subjected to special coating treatment to prevent the liquid sample from being left, there was a problem that the cost of manufacturing the device is increased, but according to the present invention, since the special coating treatment itself may be excluded, there is also an economic effect of eliminating such an additional cost increase problem.

DETAILED DESCRIPTION OF MAIN ELEMENTS

| | |
|---|---|
| 100: liquid sample injection apparatus | |
| 110: syringe | |
| 115: needle | 115a: discharge hole |
| 120: liquid injection part | |
| 121: body part | 122: container connection part |
| 123: syringe connection part | 124: septum |
| 125: penetration path | |
| 130: standard gas preparation device | |
| 131: diluted gas cylinder | 132: gas transfer passage |
| 133: control valve | |

BEST MODE

Hereinafter, a liquid sample injection apparatus and injection method for preparation of standard gas according to the present invention having the configuration as described above will be described in detail with reference to the accompanying drawings.

Figure 1:
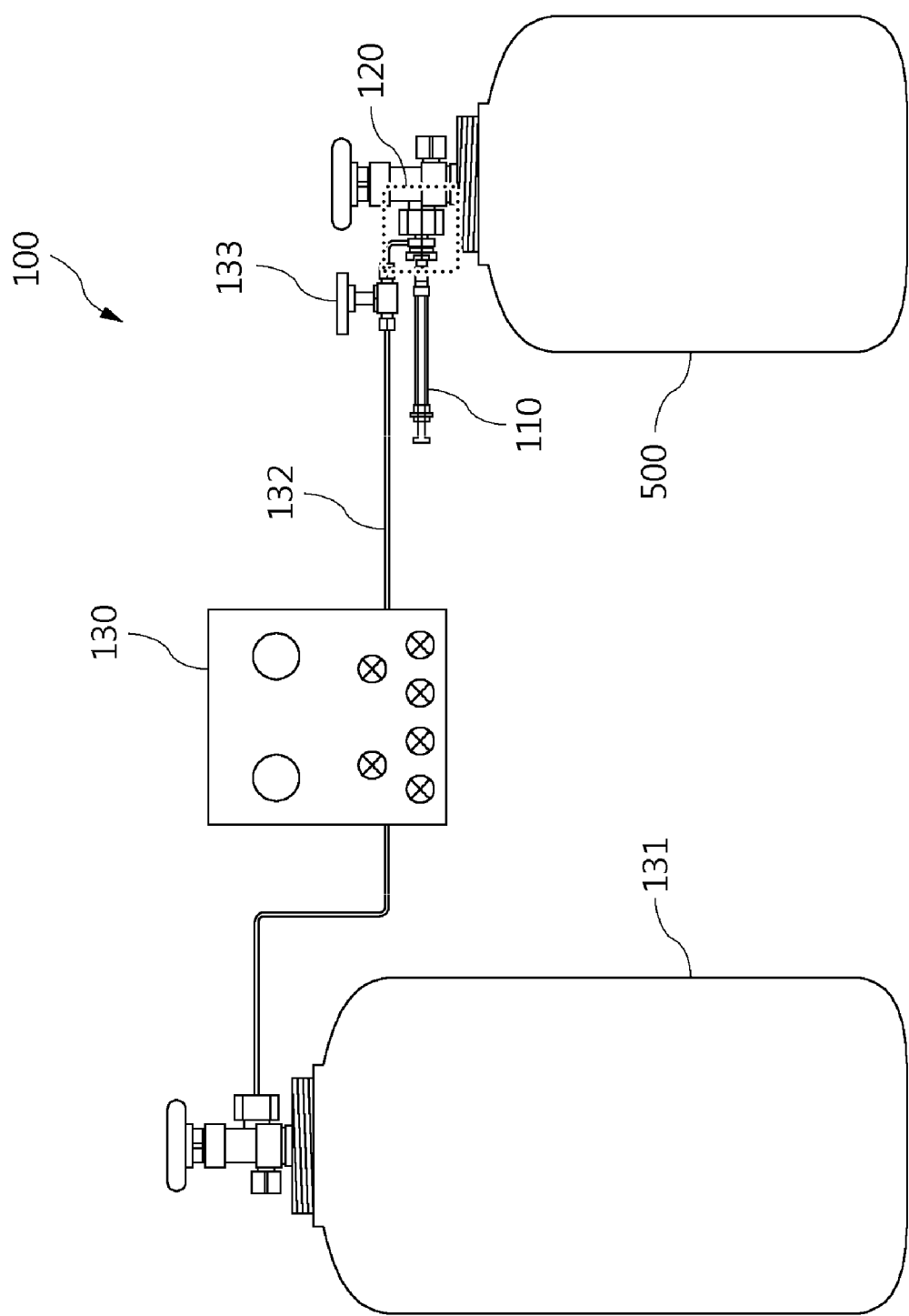
FIG. 1 is a configuration view of a injection apparatus for liquid for standard gas production according to the present invention.
Figure 2:
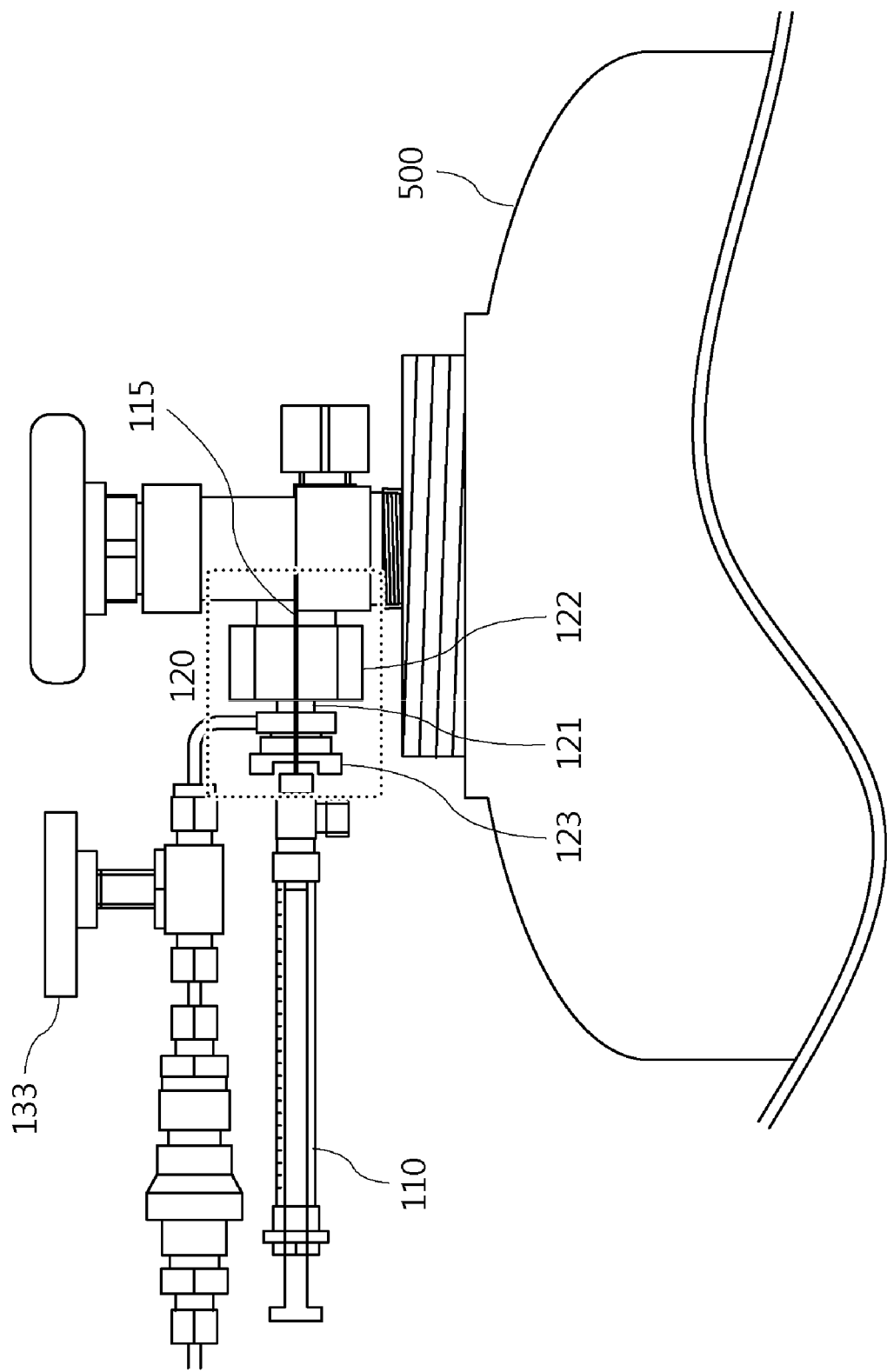
FIG. 2 is an enlarged view of a liquid injection part.
Figure 3:
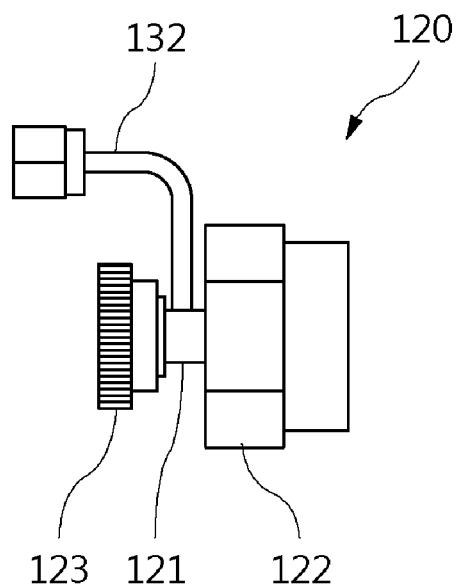
FIG. 3 is a detailed exploded view of the liquid injection part.
Figure 3:
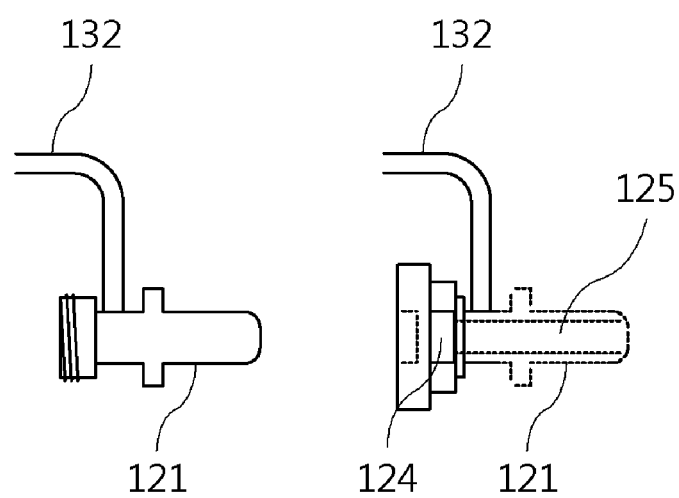
Figure 4:
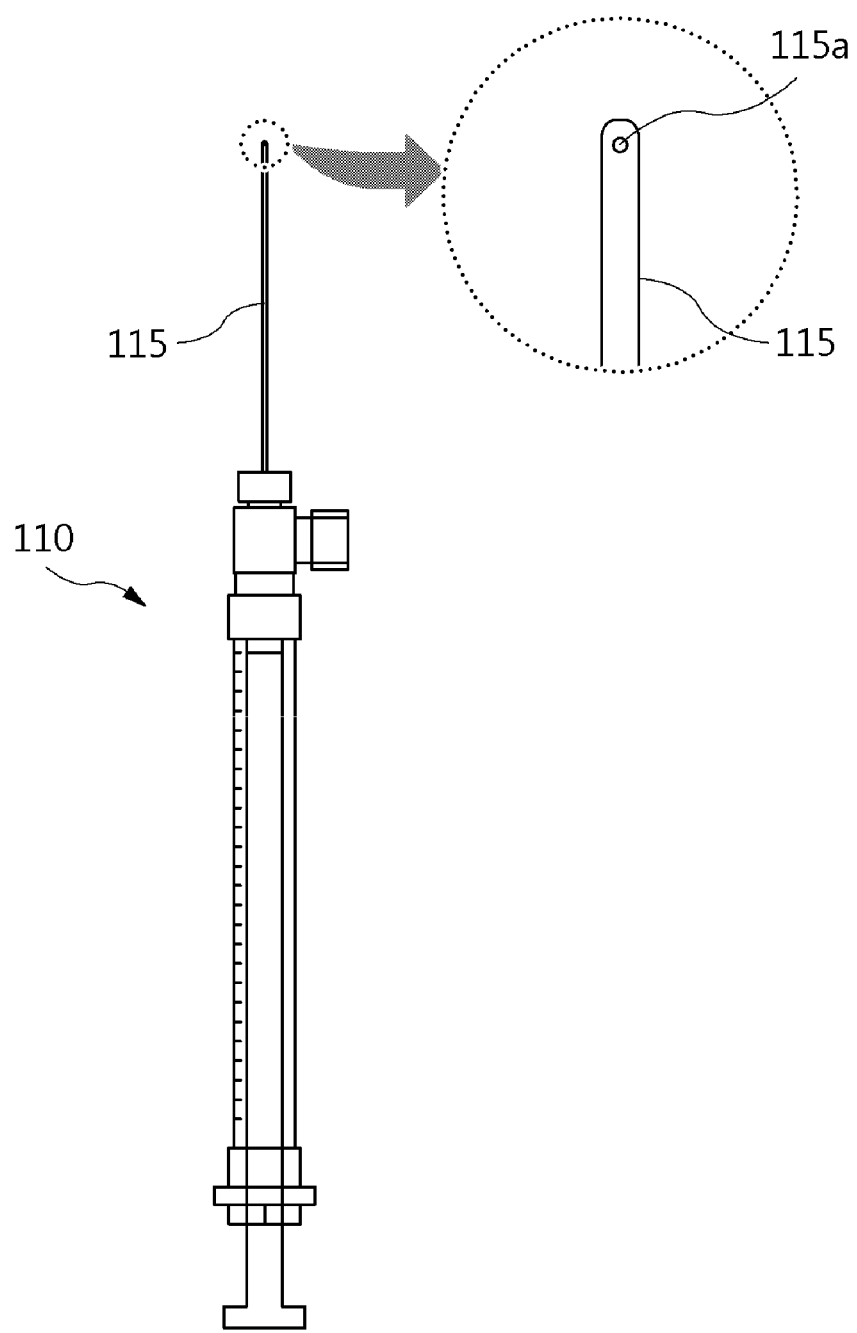
FIG. 4 is an enlarged view of a syringe.

FIG. 1 is a configuration view of a injection apparatus for liquid for standard gas production according to the present invention. In addition, FIG. 2 is an enlarged view of a liquid injection part, FIG. 3 is a detailed exploded view of the liquid injection part, and FIG. 4 is an enlarged view of a syringe. A configuration of a injection apparatus for liquid for standard gas production according to the present invention will be described with reference to FIGS. 1 to 4, and a injection method for liquid for standard gas production according to the present invention will be described based on the configuration of the injection apparatus for liquid for standard gas production.

Overall Configuration of Liquid Sample Injection Apparatus According to the Present Invention A liquid sample injection apparatus 100 for preparation of standard gas according to the present invention is a device connected to an inlet of a standard gas container 500 to supply a liquid sample and a diluting gas to the standard gas container 500 and gasifying the liquid sample to inject the gasified liquid sample into the standard gas container 500, as basically described above with reference to the related art. The liquid sample injection apparatus 100 is configured to include a syringe 110, a liquid injection part 120, a standard gas preparation device 130, as illustrated in FIG. 1.

The syringe 110 is configured to include a needle 115 and serves to inject a liquid sample. As described above, the liquid sample injection apparatus 100 according to the present invention is optimally applied to a case in which a raw material of a standard gas to be prepared exists in a liquid state at room temperature and has strong volatile property. Such a raw material is often kept in a liquid state in a reagent bottle in a sealed state (to prevent volatilization), and thus it is easy to collect the liquid sample from such a reagent bottle by using the syringe 110.

The liquid injection part 120 is connected to the inlet of the standard gas container 500 that extends in a vertical direction to form a structure that allows the liquid sample to be smoothly injected into the standard gas container 500. The liquid injection part 120 is particularly, provided with a penetration path 125 that extends in a horizontal direction and is in communication with the inlet of the standard gas container 500. Accordingly, the needle 115 may easily penetrate through the liquid injection part 120, to allow a tip of the needle 115 to be directly disposed in the inlet of the standard gas container 500. Most preferably, the needle 115 is disposed so that the tip of the needle 115 inserted into the inlet of the standard gas container 500 is positioned at the center of the inlet of the standard gas container 500.

The standard gas preparation device 130 is connected to the inlet of the standard gas container 500 through a gas transfer passage 132 which is in communication with the penetration path 125. The standard gas preparation device 130 serves to inject the diluting gas supplied from the diluting gas cylinder 131 or to perform vacuum evacuation of the standard gas container 500. The gas transfer passage 132 is preferably provided with a control valve 133 for controlling the injection of diluting gas or the performance of the vacuum evacuation.

Detailed Configuration of Liquid Sample Injection Apparatus According to the Present Invention As described above, the liquid sample injection apparatus 100 according to the present invention injects the liquid sample into the stand gas container 500 by using the syringe 110 and the liquid injection part 120 and injects the diluting gas into the stand gas container 500 by using the stand gas preparation device 130 to thereby consequently ensure that the mixture of volatilized and gasified sample gas and diluting gas is securely filled in the standard gas container 500.

Hereinafter, the configuration differences between the liquid sample injection apparatus according to the related art described above and the liquid sample injection apparatus 100 according to the present invention, and the differential effects thus obtained will be described in detail with reference to comparative drawings.

FIG. 3 is a detailed exploded view of the liquid injection part according to the present invention. As illustrated in FIG. 3, the liquid injection part 120 according to the present invention is configured to include a body part 121 having the penetration path 125 formed therein, a container connection part 122 connecting one end of the body part 121 and the inlet of the stand gas container 500 to each other, and a syringe connection part 123 connecting the other end of the body part 121 and the syringe 110 to each other. The syringe connection part 123 may be formed in the form of a lock nut as illustrated, and particularly, a septum 124 may be embedded in the syringe connection part 123. The septum 124 is formed with a through hole at the center thereof so that the needle 115 penetrates therethrough, but is formed of an elastic material such as rubber or the like, thereby sealing the vicinity of the needle 115 and preventing the volatilized liquid gas from leaking to the outside.

Although the liquid sample injection apparatus according to the related art described above is configured to be able to inject the liquid sample and the diluting gas as described above, the liquid sample injection apparatus according to the related art is configured to have a heating device in a path in which the liquid sample is injected so that the liquid sample left in a component of the injection apparatus is completely injected while being volatilized by heating. However, in the heating process as described above, there is a possibility that the components of the device are excessively heated, and particularly, sealing components such as the septum and the like formed of rubber have a risk of being damaged by such overheating. However, in the liquid sample injection apparatus 100 according to the present invention, since the heating device among the configurations of the liquid injection part 120 is originally excluded as illustrated in FIG. 3, it is possible to originally prevent the damage on the component (particularly, the sealing component such as the septum) by such heating.

Figure 5A:
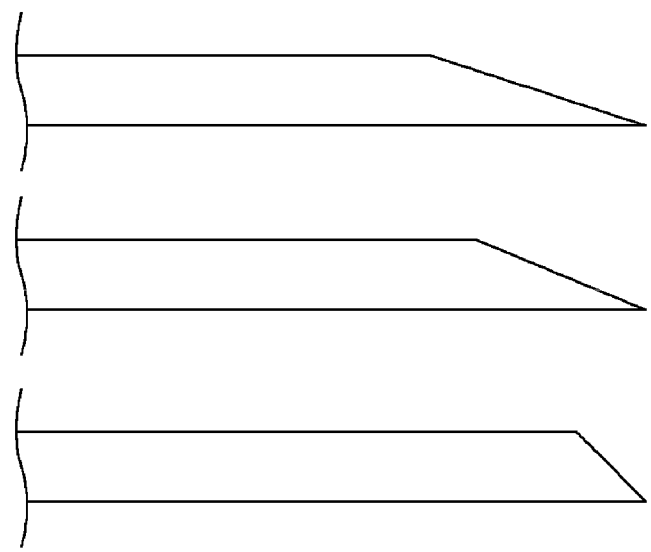
FIGS. 5A and 5B are comparative views of a needle of an injection apparatus according to the related art and a needle of an injection apparatus according to the present invention.
Figure 5B:
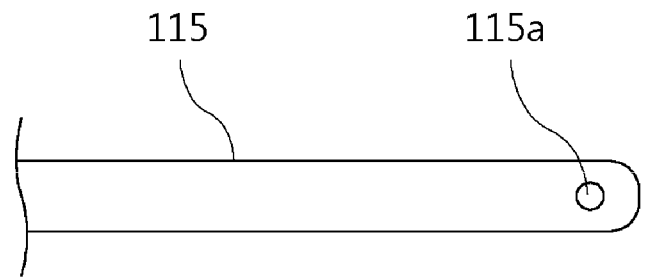

Meanwhile, in the liquid injection part 120, as illustrated in FIGS. 1 to 3, the needle 115 is disposed to completely penetrate through the liquid injection part 120. FIG. 4 is a detailed enlarged view of a syringe, particularly, a needle portion according to the present invention and FIGS. 5A and 5B are comparative views of a needle of an injection apparatus according to the related art and a needle of an injection apparatus according to the present invention. In addition, FIGS. 6A and 6B are comparative views of a configuration of an injection apparatus according to the related art and a configuration of an injection apparatus according to the present invention.

As illustrated in FIG. 5A, the needle of the injection apparatus according to the related art has an opened tip and is in the form of a common syringe needle that is sharpened to facilitate piercing. However, as illustrated in FIGS. 4 and 5B, the needle 115 according to the present invention is formed in the form of a tube having a closed tip inserted into the inlet of the standard gas container 500, and the tip is provided with a discharge hole 115*a*.

Figure 6A:
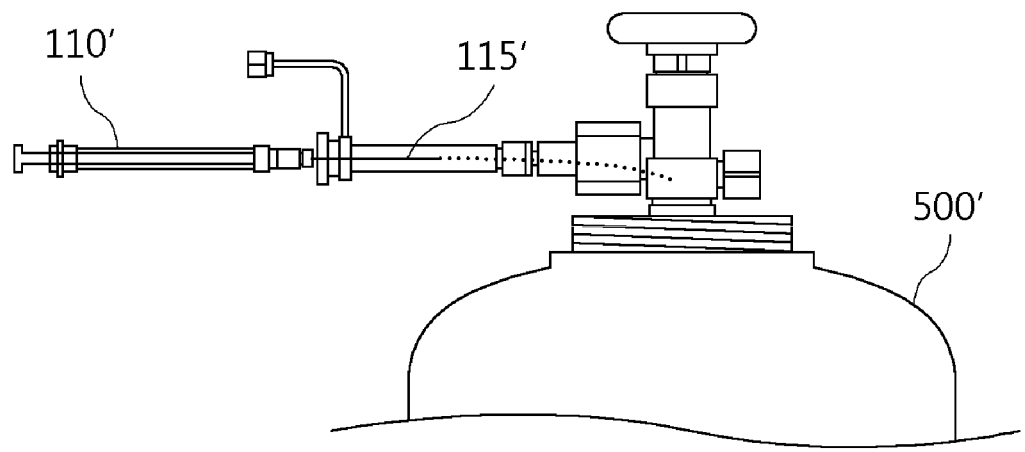
FIGS. 6A and 6B are comparative views of a configuration of an injection apparatus according to the related art and a configuration of an injection apparatus according to the present invention.
Figure 6B:
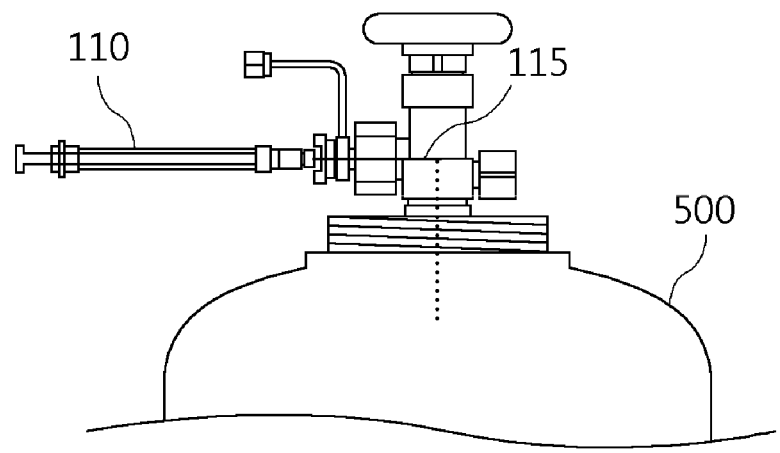

The needle 115 formed in such a form is disposed so that the tip of the needle 115 inserted into the inlet of the standard gas container 500 is positioned at the center of the inlet of the standard gas container 500, as illustrated in FIG. 6B. In addition, the discharge hole 115*a* is disposed to be formed below the tip of the needle 115 so as to downward vertically discharge the liquid sample.

As illustrated in FIG. 6A, according to the related art, when the liquid sample is discharged from a needle 115' of a syringe 110', the liquid sample passes through a passage in the connection component 120' connected to an inlet of a standard gas container 500' (corresponding to the liquid injection part). During such a process, there is a problem that the liquid sample is deposited on an inner passage of the connection component 120' and is left to be adsorbed. An injection amount of the liquid sample is measured by using a difference in syringe mass before and after injection of the liquid sample. However, as described above, when the liquid sample is left in the inner passage of the connection component 120', an amount of the liquid sample which is actually injected into the standard gas container and an amount of the liquid sample calculated to be injected as the measurement do not match each other, which results in lower accuracy of a standard gas preparation concentration.

Conventionally, in order to solve such a problem, (although not illustrated in FIG. 6A), as described above, the heating device is provided to surround the connection component 120', and the liquid sample that is left in the inner passage of the connection component 120' is volatilize and gasified by the heat transmitted from the heating device so that the liquid sample may be completely injected into the standard gas container 500'. However, another problem occurs that there is a risk of damaging the sealing component as described above in the process of heating According to the present invention, the needle 115 completely penetrates through the liquid injection part 120 and the tip of the needle 115 is disposed at the inlet of the standard gas container 500, thereby completely solving the above-mentioned problems. As described above, according to the present invention, the tip of the needle 115 is disposed at the center of the inlet of the standard gas container 500, and the liquid sample is discharged through the discharge hole 115a formed in the tip of the needle 115.

That is, since the liquid sample is not in contact with the inside of the liquid injection part 120 (for example, the penetration path 125), the cause of [the problem that the liquid sample is left in the injection apparatus] is originally removed. In addition, accordingly, the necessity of forcibly volatilizing the left liquid sample is eliminated, thereby making it possible to eliminate the heating device, and the cause of [the problem that the sealing component is damaged by heating] is also originally removed. Further, conventionally, in order to prevent the liquid sample from being left as much as possible, the special coating treatment is applied to the inner passage of the connection component 120' so as to prevent the adsorption of the liquid sample and there is the problem that a considerable cost occurs in such a special coating treatment, but according to the present invention, the above-mentioned cost increase problem may also be originally eliminated.

As well, as illustrated in FIG. 6B, in the case in which the discharge hole 115a formed in the tip of the needle 115 according to the present invention is disposed downward vertically, since the liquid sample is discharged downward vertically, that is, into only the inside of the standard gas container 500, it is possible to completely eliminate an additional possibility that the liquid sample is deposited and is left on a cap for blocking the inlet and the like.

Figure 7A:
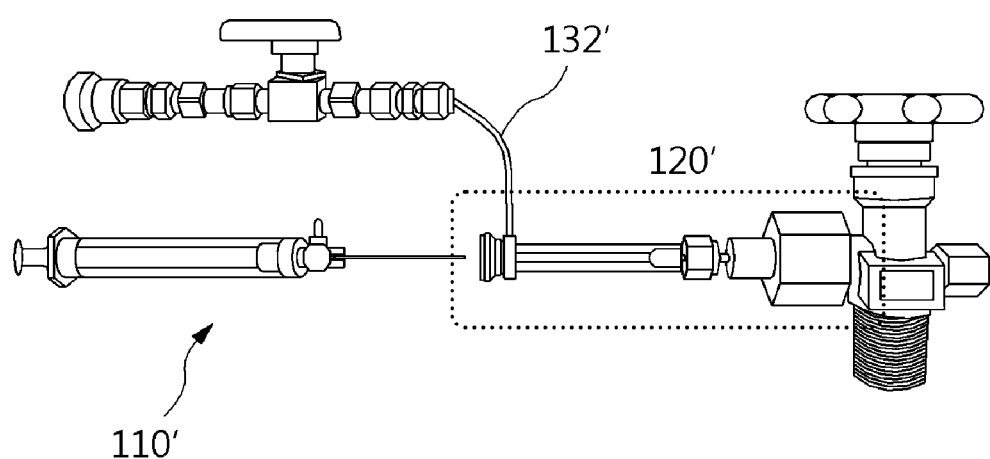
FIGS. 7A and 7B are comparative views of actual products of an injection apparatus according to the related art and an injection apparatus according to the present invention.
Figure 7B:
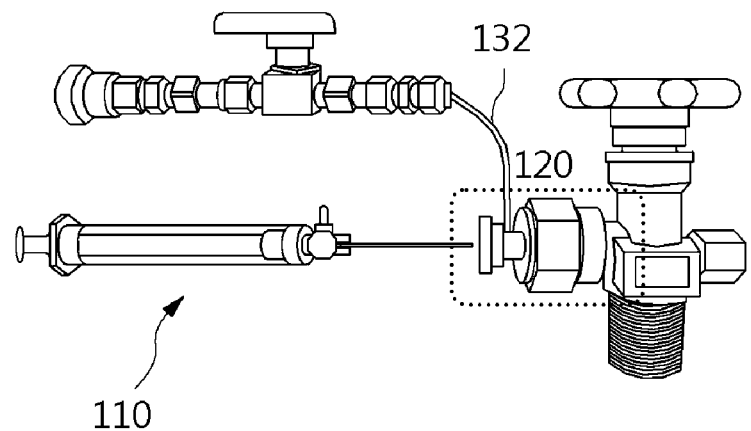

FIGS. 7A and 7B illustrate comparative views of actual products of an injection apparatus according to the related art and an injection apparatus according to the present invention. As illustrated in FIG. 7A, in the injection apparatus according to the related art, the connection component 120' is formed to be significantly long so as to have the heating device therearound. However, in the injection apparatus according to the present invention, as illustrated in FIG. 7B, the liquid injection part 120 is formed to be very short. By forming the injection apparatus as described above, the liquid sample injection apparatus 100 according to the present invention may also obtain an additional advantage that an overall volume of the device may be reduced.

Flow of Liquid Sample Injection Method According to the Present Invention

Hereinafter, the liquid sample injection method according to the present invention using the liquid sample injection apparatus 100 according to the present invention as described above will be described sequentially.

First, the liquid injection part 120, the standard gas preparation device 130, and the standard gas container 500 are evacuated. As described above, the standard gas preparation device 130 may also inject the diluting gas and may also perform the vacuum evacuation, and such an operation may be smoothly implemented by allowing the liquid injection part 120 and the standard gas container 500 to be in communication with the standard gas preparation device 130 and then operating the standard gas preparation device 130 to perform the vacuum evacuation.

Next, a liquid sample is collected in the syringe 110. The liquid sample is stored in a separate sample container in a state in which it is contained in the separate sample container, and the collection of the liquid sample may be easily completed by piercing the needle 115 into the sample container and sucking the liquid sample into the syringe 110.

Next, after the liquid sample is collected, the needle 115 of the syringe 110 is replaced. The liquid sample is deposited and is left in the needle 115 used for collecting the liquid sample in the process of collecting the liquid sample, which may cause error in measuring an exact mass of the liquid sample. According to the present invention, such an error cause is removed through an operation of replacing the needle 115 used for collecting the liquid sample (that is, in which the liquid sample is left) with a new needle after the liquid sample is collected.

Next, a mass of the syringe 110 in which the liquid sample is contained is measured. In this case, the measured mass is [liquid sample+syringe] mass.

Next, the needle 115 is inserted into the penetration path 125 of the liquid injection part 120 to position the tip of the needle 115 in the inlet of the standard gas container 500. Most preferably, as illustrated in FIG. 6B, the tip of the needle 115 is positioned at the center of the inlet of the standard gas container 500, and the discharge hole 115a of the needle 115 is disposed toward inside the standard gas container 500, that is, vertically downward of the standard gas container 500.

Next, the needle 115 is evacuated. The liquid injection part 120, the standard gas preparation device 130, and the standard gas container 500 are in the evacuated state by performing the vacuum evacuation using the standard gas preparation device 130 in the first operation, but external atmosphere is left in a space in the needle 115. Since the external atmosphere is also an impurity in the viewpoint of the standard gas preparation, the standard gas preparation device 130 performs the vacuum evacuation to evacuate the space in the needle in order to completely remove the external atmosphere.

Next, the liquid sample contained in the syringe 110 is volatilized and gasified while being injected into the standard gas container 500. As described above, since the insides of the liquid injection part 120, the standard gas preparation device 130, and of the standard gas container 500 are evacuated in the first operation and the space in the needle 115 is also evacuated in the immediately preceding operation, the liquid sample is sprayed in the completely evacuated space. Therefore, the liquid sample is easily gasified by high volatility of the liquid sample itself and is smoothly filled in the standard gas container 500 as sample gas in a gas form. In addition, since the space into which the liquid sample is injected is evacuated well, the liquid sample in the needle 115 may be completely smoothly sucked into the standard gas container 500 even though an additional process such as separate heating or the like as in the related art is not performed.

Next, after the liquid sample is injected, the mass of the syringe 110 is measured and an injection amount of the liquid sample is calculated. As described above, the mass of the liquid sample measured in the state of the syringe 110 is the mass of [liquid sample+syringe], and the mass measured after the liquid sample is injected is a mass of a completely empty [syringe] (because the entire amount of the liquid sample is completely sucked into the standard gas container 500 in the immediately preceding operation). Therefore, an exact mass of the liquid sample injected into the standard gas container 500 may be calculated by subtracting a mass value of [syringe] measured at the present operation from a mass value of the [liquid sample+syringe] which is measured previously. In addition, as described above, according to the present invention, since all of the causes of the error are originally removed by replacing the needle after the liquid sample is collected, adopting a configuration in which the liquid sample is not in direct contact with any component in the injection apparatus other than the needle, or performing the operation of completely evacuating the liquid sample that may also be left in the needle using the space evacuation to prevent the liquid sample from being left in any component in the injection apparatus including the needle, the injection amount of the liquid sample calculated in such a manner has a much more accurate value than in the related art.

Next, the diluting gas is injected into the standard gas container 500 through the standard gas preparation device 130 such that a mixed gas of the sample gas and the diluting gas is filled in the standard gas container 500. Thereafter, when the standard gas container 500 is completely sealed and a mass thereof is measured, a mass of [sample gas+diluting gas+standard gas container] may be calculated, and a mass of [diluting gas] may also be calculated by subtracting a mass of [standard gas container] which is measured in advance and a mass of [sample gas], which is the same mass as the injection amount of the liquid sample measured in the previous operations. Thereby, a sample gas concentration of the mixed gas filled in the standard gas container 500 may be accurately calculated.

The present invention is not limited to the abovementioned exemplary embodiments, but may be variously applied. In addition, the present invention may be variously modified by those skilled in the art to which the present invention pertains without departing from the gist of the present invention claimed in the claims.

INDUSTRIAL APPLICABILITY

According to the present invention, it is possible to effectively remove the problem that the liquid sample is adsorbed or left in the injection apparatus when the liquid sample is injected into the standard gas container, and as a result, accuracy of the prepared sample may be increased. Further, there is also an economical effect of reducing the preparation cost by eliminating the special coating treatment or the like for preventing the conventional problem that the liquid sample is left.

The invention claimed is:

1. An injection apparatus for liquid for standard gas production that is connected to an inlet of a standard gas container to supply a liquid sample and diluting gas to the inlet of the standard gas container and gasifies the liquid sample to inject the gasified liquid sample to the standard gas container, the injection apparatus for liquid for standard gas production comprising:
  a syringe including a needle to inject the liquid sample;
  a liquid injection part connected to the inlet of the standard gas container extending in a vertical direction, and including a penetration path extending in a horizontal direction so that the needle penetrates therethrough and communicating with the inlet of the standard gas container; and
  a standard gas preparation device connected to the inlet of the standard gas container through a gas transfer passage which is in communication with the penetration path to inject a diluting gas supplied from a diluting gas cylinder or to perform a vacuum evacuation of the standard gas container,
  wherein the needle is disposed such that a tip of the needle inserted into the inlet of the standard gas container is positioned such that the tip of the needle is directly at the inlet of the standard gas container.

2. The injection apparatus for liquid for standard gas production of claim 1, wherein the needle is disposed so that a tip thereof inserted into the inlet of the standard gas container is positioned at the center of the inlet of the standard gas container.

3. The injection apparatus for liquid for standard gas production of claim 1, wherein the needle is formed in the form of a tube having a closed tip inserted into the inlet of the standard gas container, and the tip is provided with a discharge hole.

4. The injection apparatus for liquid for standard gas production of claim 3, wherein the discharge hole is formed below the tip of the needle so as to downward vertically discharge the liquid sample.

5. The injection apparatus for liquid for standard gas production of claim 1, wherein the liquid injection part includes:
  a body part having the penetration path formed therein,
  a container connection part connecting one end of the body part and the inlet of the stand gas container to each other, and
  a syringe connection part connecting the other end of the body part and the syringe to each other.

6. The injection apparatus for liquid for standard gas production of claim 5, wherein the liquid injection part further includes a septum embedded in the syringe connection part and having a through hole formed at the center thereof so that the needle penetrates therethrough to perform sealing.

7. The injection apparatus for liquid for standard gas production of claim 5, wherein the syringe connection part is formed in the form of a lock nut.

8. The injection apparatus for liquid for standard gas production of claim 1, wherein the gas transfer passage is provided with a control valve for controlling the injection of diluting gas or the performance of the vacuum evacuation.

9. An injection method for liquid for standard gas production using an injection apparatus that is connected to an inlet of a standard gas container to supply a liquid sample and diluting gas to the inlet of the standard gas container and gasifies the liquid sample to inject the gasified liquid sample to the standard gas container, the injection apparatus for liquid for standard gas production comprising:
- a syringe including a needle to inject the liquid sample;
- a liquid injection part connected to the inlet of the standard gas container extending in a vertical direction, and including a penetration path extending in a horizontal direction so that the needle penetrates therethrough and communicating with the inlet of the standard gas container; and
- a standard gas preparation device connected to the inlet of the standard gas container through a gas transfer passage which is in communication with the penetration path to inject a diluting gas supplied from a diluting gas cylinder or to perform a vacuum evacuation of the standard gas container, the injection method for liquid for standard gas production comprising:
- evacuating the liquid injection part, the standard gas preparation device, and standard gas container;
- collecting the liquid sample in the syringe;
- replacing the needle of the syringe;
- measuring a mass of the syringe in which the liquid sample is contained;
- inserting the needle into the penetration path of the liquid injection part to position the tip of the needle in the inlet of the standard gas container;
- evacuating the needle;
- volatilizing and gasifying the liquid sample contained in the syringe while injecting into the standard gas container;
- calculating an injection amount of the liquid sample by measuring the mass of the syringe after the liquid sample is injected; and
- injecting the diluting gas into the standard gas container through the standard gas preparation device.

* * * * *